US00PP10198P

United States Patent [19]

Heimos

[11] Patent Number: Plant 10,198

[45] Date of Patent: Jan. 13, 1998

[54] POINSETTIA PLANT NAMED '9-95'

[75] Inventor: Norwin G. Heimos, St. Louis, Mo.

[73] Assignee: Paul Ecke Ranch, Inc., Encinitas, Calif.

[21] Appl. No.: 698,338

[22] Filed: Aug. 15, 1996

[51] Int. Cl.[6] ..... A01H 5/00

[52] U.S. Cl. ..... Plt./86.3

[58] Field of Search ..... Plt./86.3

[56] References Cited

U.S. PATENT DOCUMENTS

P.P. 5,497 6/1985 Deibel ..... Plt./86.3

P.P. 8,274 6/1993 Jacobsen ..... Plt./86.3

P.P. 8,817 7/1994 Fruehwirth ..... Plt./86.3

*Primary Examiner*—James R. Feyrer

*Assistant Examiner*—Kent L. Bell

*Attorney, Agent, or Firm*—Arnold, White & Durkee

[57] ABSTRACT

Poinsettia '9-95' is a new cultivar, distinguished by unique dark pink flower bracts, strong stems and self-branching characteristics. '9-95' is a sport of the pink bracted 'V-14 Hot Pink' (U.S. Plant Pat. No. 5,497) with the same flowering response and cultural requirements. The new plant produces a very desirable branched flowering pot plant. It is resistant to epinasty after being confined to shipping containers. The post-production foliage and bract retention are good.

1 Drawing Sheet

BACKGROUND OF THE INVENTION

This new poinsettia cultivar originated as a dark pink bracted natural sport of 'V-14 Hot Pink' (U.S. Plant Pat. No. 5,497) in my greenhouse in St. Louis, MO in 1994. It was selected, because of its dark pink flower bracts and strong growth habit, distinguishing it from other poinsettia cultivars. The bract color was darker and more intense than 'V-14 Hot Pink', seemingly making it more desirable for commercial greenhouse production. After selection, '9-95' was vegetatively reproduced from stem cuttings for test purposes in Encinitas, Calif. By subjecting clones of this plant to successive characteristics of '9-95' held true from generation to generation. Grown under the same greenhouse environment, '9-95' had the same growth habit and flowering response time as the parent plant 'V-14 Hot Pink'.

DESCRIPTION OF THE PHOTOGRAPHS

Poinsettia '9-95' is illustrated in the accompanying color photographs.

The upper photo is a side view of one branched plant per pot in full flower.

The lower photo is a top view of both '9-95', left and its parent 'V-14 Hot Pink', right showing the comparative flower bract colors.

DESCRIPTION OF THE PLANT

The following is a detailed description of this new poinsettia as observed in Encinitas, Calif., USA during December 1995. Observations were recorded from flowering plants, grown as one branched plant per pot. The pot was 14 cm in diameter and 11 cm in height. Color designations are compared to the 1986 edition of RHS Colour Chart, first published in 1966 by The Royal Horticultural Society, London, England.

THE PLANT

The following chart summarizes the differences between Poinsettia '9- 95' and its parent plant 'V-14 Hot Pink' (U.S. Plant Pat. No. 5,497).

| Plant | '9-95' | 'V-14 Hot Pink' |
|---|---|---|
| Flower bract color | | |
| Upper surface | RHS 58B | RHS 52C |
| Under surface | RHS 52B | RHS 48C |

Origin: Sport of 'V-14 Hot Pink' (U.S. Plant Pat. No. 5,497).

Classification:

*Botanical.*—*Euphorbia pulcherrima* Willd.

*Common name.*—Poinsettia.

*Cultivar name.*—'9-95'.

Form: Shrub.

Height: Medium.

Growth habit: As a single stemmed plant, upright and vigorous with self-branching side shoots. The application of a chemical growth retardant may be needed to restrict height for commercial pot plant production. I observed one branched plant in a pot with an overall height of 43 cm and an overall width of 53 cm. The bract diameter of individual flowers was 30 cm.

Branching: Axillary branches will develop and terminate in a flower without pinching. However, it is usually desirable to pinch '9-95' before flower induction and remove all terminal dominance. Then, all axillary branches will develop uniformly and at a faster rate.

Growth rate: Rooting of stem cuttings occurs in 12–18 days under intermittent mist.

Flowering: The plant will flower in ten weeks under continuous long night conditions and night temperatures of 16–18 degrees C. Like its parent, ('V-14 Hot Pink'), '9-95' will be in full bloom in early December in the northern hemisphere under natural day length conditions.

Foliage: The foliage was clean and uniformly dark green from bottom to top of the plant. The leaves were of medium size, leaf blades typically being 13 cm long and 9 cm wide with leaf petioles 6 cm long. The upper surfaces of the leaf petiole are pinkish. The under surfaces are green.

*Leaf shape.*—Typical leaves are ovate with acute bases and acuminate tips. Leaf margins are usually lobed, with 1 or 2 lobes on either side of the leaf blade.

*Leaf surface.*—The upper surface is slightly rugose and glabrous and the under surface is slightly pubescent.

*Color.*—Upper side — Green, near RHS 147A. Under side — Green, near RHS 147B.

*Retention.*—The foliage retention was good even under low light intensities in the consumer's home.

Bracts: Generally there were 12–15 pink bracts of various sizes subtending the cyathia. The primary bracts had blades typically 13 cm long and 8 cm wide with petioles 4 cm long.

*Shape.*—Primary bracts are ovate with acute bases and acuminate tips. Leaf margins are lobed with 1–2 indentations on either side of the bract. Secondary bracts are elliptical with modest indentations in the margins.

*Surface.*—The bract surface is slightly rugose.

*Color.*—Upper side — A dark pink, near R.H.S. 58B. Under side — Pink, near R.H.S. 52B.

Flowers: Generally, 10–12 cyathia (flowers) were present when the plant was in full bloom. Each cyathium was about 7 mm long and 6 mm wide, green in color, and fringed pink at the distal end. One or sometimes two yellow nectar cups protrude from the side of each cyathium. The flower pedicel is also green and about 6 mm in length. The filaments protruding from the cyathia are pink. The stigmas are pink and trifurcate. The pollen is yellow and copious. Cyathia retention was about three weeks beyond the time the flower was fully mature.

*Nectar exudate.*—Present, abundant.

*Seed formation.*—Self-incompatible.

*Fertility.*—Not observed.

Post production: '9-95' was resistant to epinasty after being confined to shipping containers. The foliage and bract retention were good.

What is claimed is:

1. A new and distinct Poinsettia plant, substantially as herein shown and described, distinguished by its strong stems, unique dark pink flower bracts, self-branching and good leaf and bract retention in the consumer environment.

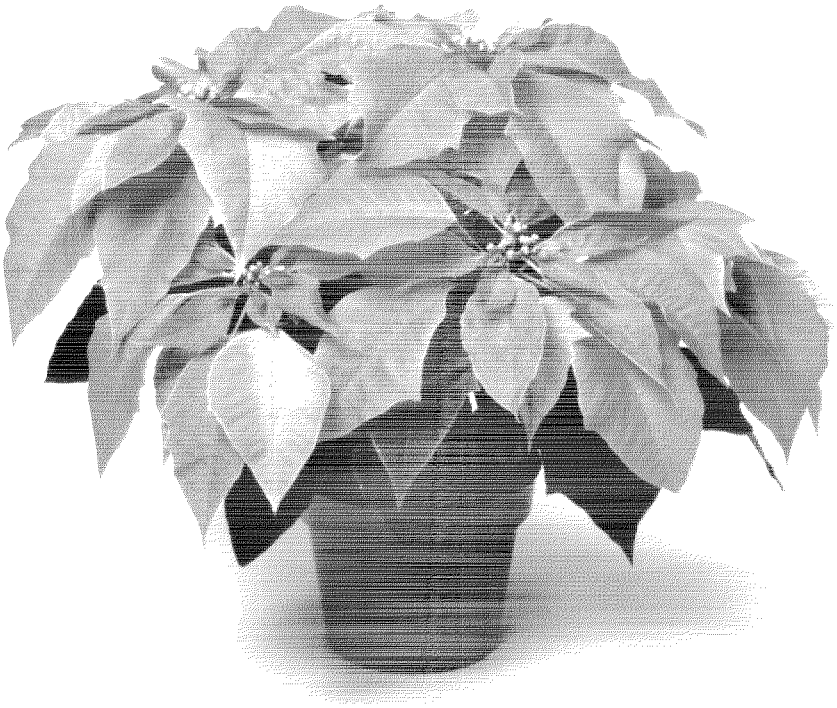
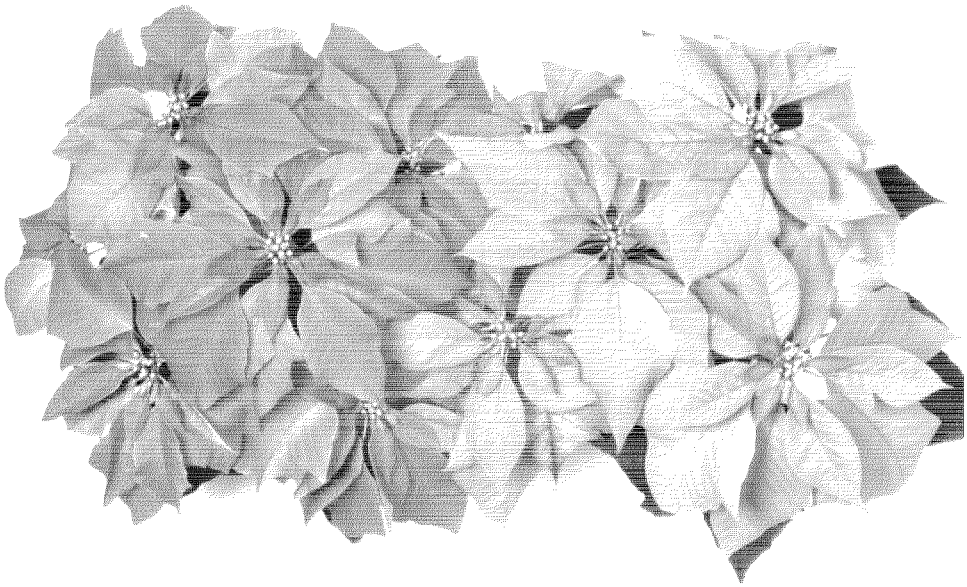

* * * * *